United States Patent [19]

Hirose et al.

[11] Patent Number: 5,536,748

[45] Date of Patent: Jul. 16, 1996

[54] HYDRAZONE COMPOUND AND INSECTICIDE CONTAINING THE SAME AS ACTIVE INGREDIENT

[75] Inventors: Taro Hirose, Takatsuki; Toshiaki Taki, Toyonaka; Hiroki Tomioka, Ikeda; Hirosi Kisida, Takarazuka; Shigeru Saito, Toyonaka, all of Japan

[73] Assignee: Sumitomo Chemical Company, Limited, Osaka-fu, Japan

[21] Appl. No.: 318,974

[22] Filed: Oct. 6, 1994

[30] Foreign Application Priority Data

Oct. 6, 1993 [JP] Japan ................. 5-250602

[51] Int. Cl.$^6$ ............. A01N 41/04; C07C 309/65; C07C 309/66
[52] U.S. Cl. ............. 514/517; 558/54; 558/58
[58] Field of Search ............. 558/54, 58; 514/517

[56] References Cited

U.S. PATENT DOCUMENTS 4,331,680  5/1982  Giles et al. .
4,344,893  8/1982  Copping et al. .

FOREIGN PATENT DOCUMENTS 0003913  9/1979  European Pat. Off. .
0254461  1/1988  European Pat. Off. .

*Primary Examiner*—Nicky Chan
*Attorney, Agent, or Firm*—Birch, Stewart, Kolasch & Birch

[57] ABSTRACT

The present invention provides a hydrazone compound of the formula I:

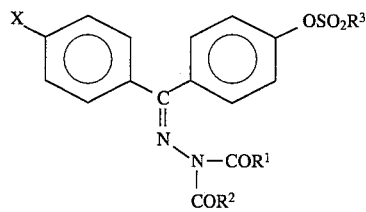

wherein $R^1$ and $R^2$ are the same or different and are independently hydrogen, $C_1$–$C_2$ alkyl, $C_1$–$C_2$ alkoxy, methoxymethyl or cyanomethyl, with the proviso that the $R^1$ and $R^2$ are not simultaneously hydrogen; $R^3$ is trifluoromethyl or methyl; and X is halogen, and an insecticide containing the hydrazone compound as an active ingredient. The hydrazone compound has good insecticidal activity and lower acute toxicity to mammals.

9 Claims, No Drawings

HYDRAZONE COMPOUND AND INSECTICIDE CONTAINING THE SAME AS ACTIVE INGREDIENT

FIELD OF THE INVENTION

The present invention relates to a hydrazone compound and an insecticide containing the same as an active ingredient.

DESCRIPTION OF THE RELATED ART

An insecticidal benzophenone-N',N'-monoacylhydrazone is disclosed in the U.S. Pat. No. 4,344,893. However, the compound is not always satisfactory for its insecticidal activity and toxicity to mammals.

SUMMARY OF THE INVENTION

Under the circumstances, the present inventors have intensively studied to obtain a compound having good insecticidal activity and lower acute toxicity to mammals. As a result, they have found that particular hydrazone compounds have good insecticidal activity and lower acute toxicity to mammals.

That is, the present invention provides a hydrazone compound of formula I:

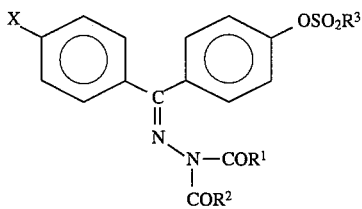

wherein $R^1$ and $R^2$ are the same or different and are independently hydrogen, $C_1$–$C_2$ alkyl, $C_1$–$C_2$ alkoxy, methoxymethyl or cyanomethyl, with the proviso that the $R^1$ and $R^2$ are not simultaneously hydrogen; $R^3$ is trifluoromethyl or methyl; and X is halogen, and an insecticide containing the hydrazone compound as an active ingredient.

PREFERRED EMBODIMENT OF THE INVENTION

For the substituents $R^1$ and $R^2$, examples of the $C_1$–$C_2$ alkyl are methyl and ethyl, and examples of the $C_1$–$C_2$ alkoxy are methoxy and ethoxy. The substituent $R^3$ is trifluoromethyl or methyl. The substituent X is halogen such as chlorine, bromine, fluorine or iodine.

The hydrazone compound of the present invention can be produced by the following production process A or B.

Production Process A

The production process A comprises reacting a compound of the formula II:

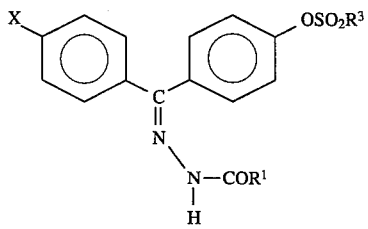

wherein $R^1$ and $R^3$ are each as defined above, with a compound of the formula III:

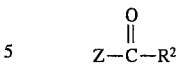

wherein $R^2$ is as defined above; Z is chlorine, bromine, a group of the formula: —$OCOR^2$, $C_1$–$C_2$ alkoxy (e.g., methoxy, ethoxy) or hydroxyl, with the proviso that when Z is hydroxyl, $R^2$ is not $C_1$–$C_2$ alkoxy.

When the compound III is an activated carboxylic acid derivative, i.e., Z is chlorine, bromine or a group of the formula: —$OCOR^2$, the reaction of the compound II with the compound III is usually carried out in the presence of a base. Examples of the base are organic bases including tertiary alkylamines such as triethylamine, ethyldiisopropylamine and tributylamine, tertiary dialkylarylamines such as N,N-diethylaniline, heteroarylamines such as pyridine compounds (e.g., pyridine, picoline and 4-(N,N-dimethylamino)pyridine); inorganic bases including alkali metal hydroxides and hydrides, such as sodium hydroxide and sodium hydride, and alkali metal carbonates such as potassium carbonate; and organometallic bases such as butyl lithium and lithium diisopropylamide.

The amount of the base to be used is usually 1 or more moles to 1 mole of the compound II.

The reaction in the process A is usually carried out in an inert organic solvent.

The solvent to be used in the process A are aromatic hydrocarbons such as benzene, toluene, xylene, chlorobenzene and o-dichlorobenzene; aromatic heteroaryl compounds such as pyridine and picoline; halogenated hydrocarbons such as chloro form, dichloromethane, carbon tetrachloride, 1,2-dichloroethane, 1,1,1-trichloroethane, tetrachloroethylene and trichloroethylene; aliphatic hydrocarbons such as n-hexane and n-heptane; alicyclic hydrocarbons such as cyclohexane; ethers such as tetrahydrofuran and diethyl ether; ketones such as acetone, methyl ethyl ketone and methyl isobutyl ketone; aprotic polar solvents such as N,N-dimethylformamide and dimethyl sulfoxide. These solvents can be used alone or in combination.

In the production process A, when Z is $C_1$–$C_2$ alkoxy, the reaction can be carried out in the presence of a catalytic amount of base. In this case, any base selected from the group consisting of the above-described bases can be used.

The reaction can be carried out in an organic solvent which is the same as described above. Furthermore, when $R^1$ and $R^2$ are the same, an alcohol such as methanol or ethanol which has the same alkoxide group as for the substituent $R^1$ may be used alone or in combination with other solvents as described above.

Alternatively, when Z in the compound III is hydroxyl, the reaction is usually carried out in the presence of a condensing agent.

As the condensing agent, any agent capable of activating a carboxyl group and/or removing water from the reactants to be condensed may be used. Examples of the condensing agent are organic acid chlorides such as tosyl chloride, pivaloyl chloride and thionyl chloride; Lewis acids such as titanium tetrachloride; and dehydrating agents such as dicyclohexylcarbodiimide, phosphorous pentoxide and polyphosphoric acid. The amount of the condensing agent to be used is usually 1 or more moles to 1 mole of the compound II.

In this case, any solvent other than alcohols described above can be used.

The amount of the compound III is usually 1 or more moles, preferably 1 to 10 moles, to 1 mole of the compound II.

The reaction temperature is usually −78° C. to 200° C., preferably −20° C. to the boiling point of the solvent used.

After completion of the reaction, the reaction product can be subjected to ordinary post-treatments such as organic solvent extraction and concentration to isolate the desired compound. If necessary, the resulting compound can be purified by a method such as chromatography and/or recrystallization.

The compound II used as the raw material can be produced by the following production process (a).

The production process (a) will hereinafter be explained in detail.

The production process (a) comprises reacting a compound of the formula IV:

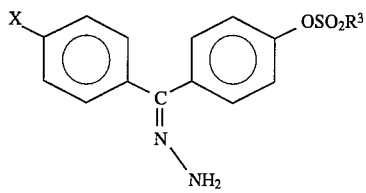

with a compound of the formula V:

wherein Z and $R^1$ are each as defined above.

When the compound V is an activated carboxylic acid derivative, i.e., Z is chlorine, bromine or a group of the formula: —$OCOR^1$, the reaction of the compound IV with the compound V is usually carried out in the presence of a base.

The base that can be used for this reaction is the same as described for the process A above.

The amount of the base to be used is usually 1 or more moles to 1 mole of the compound IV.

The reaction is usually carried out in an inert organic solvent other than ketones and alcohols used in the production process A.

In the production process (a), when Z is $C_1$–$C_2$ alkoxy, a catalytic amount of a base may be added to the reaction system. In this case, any base selected from the group consisting of the bases used in the production process A can be used.

The reaction can be carried out in an organic solvent which is the same as described above. Furthermore, an alcohol such as methanol or ethanol, which has the same alkoxide group as for the substituent R 1, can be used alone or in combination with other solvents as described above.

Alternatively, when Z is hydroxyl in the compound V, the reaction is usually carried out in the presence of a condensing agent.

In this case, any condensing agent selected from the group consisting of the condensing agents used in the production process A can be used.

The amount of the condensing agent to be used is usually 1 or more moles to 1 mole of the compound IV.

In this case, any solvent other than alcohols described above can be used.

The amount of the compound V is approximately 1 mole to 1 mole of the compound IV.

In the production process (a), the reaction temperature is usually −20° C. to the boiling point of the solvent used.

After completion of the reaction, the reaction product can be subjected to ordinary post-treatments such as organic solvent extraction and concentration to isolate the desired compound. If necessary, the resulting compound can be purified by a method such as chromatography and/or recrystallization.

The compound II produced by such a process can be used for the reaction in the production process A without isolation.

Production Process B

When $R^1$ and $R^2$ are the same, the hydrazone compound of the present invention can also be produced by the following production process B.

The production process B comprises reacting the compound IV with the compound V.

When the compound V is an activated carboxylic acid derivative, i.e., Z is chlorine, bromine or a group of the formula: —$OCOR^1$, the reaction of the compound IV with the compound V is usually carried out in the presence of a base.

The base that can be used for this reaction is the same as described for the production process A.

The amount of the base to be used is usually 2 or more moles to 1 mole of the compound II.

The reaction is usually carried out in an inert organic solvent. The solvents to be used are the same solvents other than alcohols used in the production process A.

In the production process B, when Z is $C_1$–$C_2$ alkoxy, the amount of the base may be catalytic. In this case, any base selected from the group consisting of the bases as described above can be used.

The reaction can be carried out in an organic solvent which is the same as described above. Furthermore, an alcohol such as methanol or ethanol, which has the same alkoxide group as for the substituent $R^1$ may be used or in combination with other solvents as described above.

Alternatively, when Z is hydroxyl in the compound V, the reaction is usually carried out in the presence of a condensing agent.

In this case, any condensing agent selected from the group consisting of the condensing agents used in the production process A above can be used.

The amount of the condensing agent to be used is usually two or more moles to one mole of the compound of the formula V.

In this case, any solvent other than alcohols as described above can be used.

The amount of the compound V is approximately two or more moles to one mole of the compound IV.

The reaction temperature is usually −20° C. to the boiling point of the solvent used.

After completion of the reaction, the reaction product can be subjected to an ordinary post-treatment to isolate the desired compound.

The compound IV used as the raw material for the production processes A and B can be produced, for example, by the process described in the U.S. Pat. No. 4,344,893.

The hydrazone compound of the present invention has two geometrical isomers with a C=N double bond in the hydrazone moiety. The two geometrical isomers (in E and G configurations) and mixtures thereof are included in the present invention.

The hydrazone compound of the present invention is effective for controlling various insects including:

Hemiptera:

Delphacidae (leaf hoppers) such as *Laodelphax striatellus, Nilaparvata lugens* and *Sogatella furcifera*; Cicadelloidea (leaf hoppers) such as *Nephotettix cincticeps* and *Nephotettix virescens*, Aphidoidea (ap.ids) including *Aphis*

*grossypii*, Pentatomidae (stink bugs), Aleyrodidae, Coccoidea (scale insects), Tingidae (lacebugs), Psyllidae (jumping plant-lices), etc.;

Lepidoptera:

Pyralidae such as *Chilo suppressalis, Cnaphalocrocis medinalis, Ostrinia nubilalis, Parapediasia teterrella, Notarcha derogata* and *Plodia interpunctella*; Noctuidae (owlet moths) such as *Spodoptera litura, Pseudaletia separata, Mamestra brassicae, Agrotis ipsilon*, Heliothis moths, Helicoverpa moths; Pieridae such as *Pieris rapae crucivora*; Tortricidae (bell moths) such as *Grapholita molesta* and *Cydia pomonetla, Carposina niponensis*, Lyonetiidae (leaf mining moths), Euproctis and Lymantria (gypsy) moths; Yponomeutidae such as *Plutella xylostella*; Gelechiidae such as *Pectinophora gossypiella*, Arctiidae such as *Hyphantria cunea, Tinea translucens, Tineola bisselliella*, etc.;

Diptera:

Culex (house mosquitos) such as *Culex pipiens pallens* and *Cules tritaeniorhynchus*; Aedes such as *Aedes albopictus* and *Aedes aegypti*; Anophelinae such as *Anophelinae sinensis*, Chironomidae (midges); Muscidae such as *Musca domestica* (house fly) and *Muscina stabulans*; Calliphoridae (blow flies); Sarcophagidae (flesh flies); Anthomyiidae such as *Delia platura* and *Delia antigua*, Trypetidae (fruit flies), Drosophilidae (wine flies), Psychodidae (moth flies), Tabanidae (deer flies), Simuliidae (black flies), Stomoxyinae, Agromyzidae (leaf miner flies), etc.;

Coleoptera (beetles):

Diabrotica (corn rootworms) such as *Diabrotica virgifera* and *Diabrotica undecimpunctata*; Scarabaeidae such as *Anomala cuprea* and *Anomala rufocuprea*; Curculionidae (snout beetles) such as *Sitophilus zeamais* (grain weevils) *Lissorphoptrus oryzophilus, Hypera pastica*, and *Calosobruchys chinensis, Neatus ventralis* (darkling beetles) such as *Tenebrio molitor* and *Tribolium castaneum*; Chysomelidae (leaf beetles) such as *Aulacophora femoralis, Leptinotarsa decemlineata* and *Phyllotreta striolata*; Anobiidae (death-watch beetles), Epilachna spp. such as *Henosepilachna vigintioc-topunctat*, Lyctidae (powder-post beetles), Bostrychidae (lesser grain borers), *Paederus fuscipes*, etc.;

Blattaria (cockroaches):

*Biattella germanica* (croton bugs), *Periplaneta fuliginosa, Periplaneta americana, Periplaneta brunnea, Blatta orientalis*, etc.;

Thysanoptera (thrips):

*Thrips palmi, Thrips tabaci, Thrips hawaiiensis*, etc.;

Hymenoptera:

Formicidae (ants), Vespa (hornets), Bethylidae (bethylid wasps), Tenthredinoidae (sawflies) such as Athalia rosae japonensis (cabbage sawfly), etc.;

Orthoptera:

Gryllotalpa (mole crickets), Acridoidea (grasshoppers), etc.;

Siphonaptera (fleas):

*Purex irritans*, etc.;

Anoplura (sucking louses): *Pediculus humanus capitis, Phthirus pubis* Human louse, etc.;

Isoptera (termites):

*Reticulitermes speratus, Coptotermes formosanus*, etc.; *Purex irritans* and the like;

The hydrazone compound of the present invention is also effective for various insects having resistance to conventional insecticides.

For the practical use of the hydrazone compound as an active ingredient of insecticides, acaricides or nematocides, it may be used as such; however, the hydrozone compound of the present invention is usually formulated into oil sprays, emulsifiable concentrates, wettable powders, flowables such as water suspensions or emulsions, granules, dusts, aerosols, heating fumigants such as combustible fumigants, chemical fumigants and porous ceramics fumigants, ULV (formulations for ultra low volume application) and poison baits. These formulations are usually prepared by mixing the hydrazone compound of the present invention with a solid carried, a liquid carrier, a gaseous carried or bait, and if necessary, adding a surfactant and other auxiliaries for the formulation. These formulations usually contain the hydrazone compound of the present invention as an active ingredient in an amount of 0.01% to 95% by weight.

Examples of the solid carriers to be used for the formulation are fine powder or granules of clay such as kaolin clay, diatomaceous earth, synthetic hydrated silicon oxide, bentonite and acid clay; talc, ceramics, inorganic :minerals such as sericite, quartz, sulfur, active carbon, calcium carbonate and hydrated silica; and chemical fertilizers such as ammonium sulfate, ammonium phosphate, ammonium nitrate, urea and ammonium chloride.

Examples of the liquid carrier are water; alcohols such as methanol and ethanol; ketones such as acetone and methyl ethyl ketone; aromatic hydrocarbons such as benzene, toluene, xylene, ethylbenzene and methylnaphthalene; aliphatic hydrocarbons such as hexane, cyclohexane, kerosine and gas oil; esters such as ethyl acetate and butyl acetate; nitriles such as acetonitrile and isobutyronitrile; ethers such as diisopropyl ether and dioxane; acid amides such as N,N-dimethylformamide and N,N-dimethylacetamide; halogenated hydrocarbons such as dichloromethane, trichloroethane and carbon tetrachloride; dimethyl sulfoxide; and vegetable oils such as soybean oil and cottonseed oil.

Examples of the gaseous carrier or propellant are CFCs (chlorofluoro-carbons), butane gas, LPG (liquefied petroleum gas), diethyl ether and carbon dioxide.

Examples of the surfactant are alkyl sulfates, alkyl sulfonates, alkyl arylsulfonates, alkyl aryl ethers, polyethylene glycols, polyethylene, glycol ethers, polyhydric alcohol derivatives and sugar alcohol derivatives.

Examples of the auxiliaries for the formulation, such as fixing agents or dispersing agents, are casein, gelatin, polysaccharides such as starch, gum arabic, cellulose derivatives and alginic acid, lignin derivatives, bentonite, sugars, and synthetic water-soluble polymers such as polyvinyl alcohol, polyvinyl pyrrolidone and polyacrylic acid.

Examples of the stabilizer are PAP (isopropyl acid phosphate), BHT (2,6-di-t-butyl-4-methylphenol), BHA (mixture of 2-t-butyl-4-methoxyphenol and 3-t-butyl-4-methoxyphenol), vegentable oils, mineral oils, surfactants, fatty acids and esters of fatty acids.

Examples of the base material to be used in the combustible fumigant are exothermic agents such as nitrates, nitrites, guanidine salts, potassium chlorate, nitro-cellulose, ethylcellulose or wood powder; pyrolytic stimulating agents such as alkaline metal salts, alkaline earth metal salts, dichromates or chromates; oxygen sources such as potassium nitrates; combustion assistants such as melamine or wheat starch; bulk fillers such as diatomaceous earth; and binding agents such as synthetic glue.

Examples of the base material to be used in the chemical fumigant are exothermic agents such as alkaline metal sulfides, polysulfides, hydrogensulfides, hydrated salts or calcium oxide; catalytic agents such as carbonaceous substances, iron carbide or activated clay; organic foaming agents such as azodicarboxyamide, benzene-sulfonylhydrazide, N,N'-dinitrosopentamethylenetetramine, polystyrene or polyurethane; and fillers such as natural and synthetic fibers.

Examples of the base material to be used in the poison baits are bait materials such as grain powder, purified vegetable oil, sulfur or crystalline cellulose; antioxidants such as dibutylhydroxytoluene or nordihydroguaiaretic acid; preservatives such as dehydroacetic acid; substances for preventing erroneous eating, such as red pepper powder, attractant flavors such as cheese flavor or onion flavor.

The flowables such as water suspensions and emulsions are usually obtained by finely dispersing the hydrazone compound of the present invention at a ratio of 1% to 75% in water containing a 0.5% to 15% dispersing agent, a 0.1% to 10% suspension assistant (e.g., protective colloid or a thixotropy-giving compound) and 0% to 10% additives (e.g., antifoamers, stabilizers, bactericides, rust preventive agents, antimolds, developing agents, penetrating assistants and antifreezing agents).

The hydrazone compound of the present invention may be dispersed in oil having substantially no solubility thereof, to form oil suspensions. Examples of the protective colloid are casein, gelatin, gums, cellulose ethers and polyvinyl alcohol. Examples of the thixotropy-giving compound are bentonite, aluminum magnesium silicate, xanthan gum or polyacrylic acid.

The formulation thus obtained is used as such or after dilution with water. The formulations of the present invention may be used together with other insecticides, acaricides, nematocides, bactericides, herbicides, plant growth regulators, synergists, fertilizers and/or soil conditioners under non-mixing conditions or pre-mixing conditions.

Examples of the insecticide, acaricide and/or nematocide to be used are organophosphorus compounds such as Fenitrothion [(O,O-dimethyl O-(3-methyl-4-nitrophenyl)phosphorothionate], Fenthion [O,O-dimethyl O-(3-methl-4-methylthiophenyl)phophorothionate], Diazinon (Dimpylate) [O,O-diethyl-O-2-isopropyl-6-methylpyrimidin-4-ylphosphorothioate], Chlorpyriphos [O,O-dimethyl-O-3,5,6-trichloro-2 -pyridylphosphorothioate], Acephate [O,S-dimethyl acetylphosphoramidothioate], Methidachion (DMTP) [S-2,3-dihydro-5-methoxy-2-oxo-1,3,4-thiadiazol-3-ylmethyl O,O-dimethylphosphorothiolothionate], Disulfoton [O,O-diethyl S-2-ethylthioethyl phosphorothiolothionate], Dichlorvos (DDVP) [2,2-dichlorovinyl dimethylphosphate], Sulprofos [O-ethyl O-4-methylthiophenyl S-propyl phosphorodithioate], Cyanophos [O-4-cyanophenyl-O,O-dimethylphosphorothioate], Dioxabenzofos [2 -methoxy-4H-1,3,2-benzodioxaphosphorin 2-sulfide], Dimethoate [O,O-dimethyl-S-(N-methylcarbamoylmethyl)phosphordithioate], Phenthoate [S-ethoxycarbonylbenzyldimethyl phosphorothiolothionate], Malathion [1,2-bis(ethoxylcarbonyl)-ethyl O,O-dimethyl phosphorothiolothionate], Trichlorfon (Metrifonate) [dimethyl 2,2,2-trichloro-1-hydroxyethylphosphonate], Azinphos-methyl [S-(3,4-dihydro-4-oxo-1,2,3-benzotriazine-3-ylmethyl)dimethyl phosphorothiolothionate], Monocrotophos [cis-3-(dimethyxphosphinyloxy)-N-methylcrotonamide] and Ethion [O,O,O',O'-tetraethyl-S,S'-methylenebis(phosphorothiolothionate)].

Other examples are carbamate compounds such as BPMC [2-sec-butylphenyl methyl carbamate], Benfuracarb [ethyl N-(2,3-dihydro-2,2-dimethylbenzofuran-7-yloxycarbonyl (methyl)aminothio)-N-isopropyl-β-alaninate], Propoxur (PHC) [2-isopropoxyphenyl N-methyl carbamate], Carbosulfan [2,3-dihydro-2,2-dimethyl-7-benzo[b]furanyl N-dibutylaminothio-N-methyl carbamate], Carbaril [1-naphthyl N-methylcarbamate], Methomyl [S-methyl-N-((methylcarbamoyl)oxy)thioacetoimidate], Ethiofencarb [2-(ethylthiomethyl)phenyl methylcarbamate], Aldicarb [2-methyl.-2-(methylthio )propanaldehyde O-(methylcarbamoyl)oxime], Oxamyl [N,N-dimethyl 2-methylcarbamoyloxyimino-2-(methylthio)acetamide] and Fenothiocarb [S-4-phenoxybutyl) N,N-dimethylthiocarbamate].

Other examples are pyrethroid compounds such as Etofenprox [2-(4-ethoxyphenyl)-2-methylpropyl-3-phenoxybenzyl ether], Fenvalerate [(RS)-α-cyano-3-phenoxybenzyl (RS)-2-(4-chlorophenyl)-3-methylbutyrate], S-Fenvalerate [(S)-α-cyano-3-phenoxybenzyl (S)-2-(4-chlorophenyl)-3-methylbutyrate], Fenpropathrin [(RS)-α-cyano-3-phenoxybenzyl 2,2,3,3-tetramethylcyclopropanecarboxylate], Cypermethrin [(RS)-α-cyano-3-phenoxybenzyl (1RS,3RS)-3-(2,2-dichlorovinyl)-2,2-dimethylcyclopropanecarboxylate], Permethrin [3-phenoxybenzyl (1RS,3RS)-3-(2,2-dichlorovinyl)-2,2-dimethylcyclopropanwecarboxylate], Cyhalothrin [(RS)-α-cyano-3-phenoxybenzyl (Z)-(1RS)-cis-3-(2-chloro-3,3,3-trifluoropropen-1-yl)-2,2-dimethylcyciopropane carboxylate], Deltamethrin [(S)-α-cyano-3-phenoxybenzyl (1R,3R)-3-(2,2-dibromovinyl)-2,2 -dimethylcyclopropanecarboxylate], Cycloprothrin [(RS)-α-cyano-3-phenoxybenzyl (RS)-2,2-dichloro-1-(4-ethoxyphenyl)cyclopropanecarboxylate], Fluvalinate [α-cyano-3-phenoxybenzyl N-(2-chloro-α,α,α-trifluoro-p-tolyl)-D-valinate], Bifenthrin [2-methylbiphenyl-3-ylmethyl) (Z)-(1RS)-cis-3-(2-chloro-3,3,3-trifluoropropen-1-yl)-2,2 -dimethylcyclopropanecarboxylate], Acrinathrin [(S)-(α)-cyano-(3-phenoxyphenyl)methyl (1R)-(1α(S*),3α(Z))-2,2-dimethyl-3-(3-oxo-3-(2,2,2-trifluoro-1-methyl)ethoxy-1-propenyl)cyclopropanecarboxylate], 2-methyl-2-(4-bromodifluoromethoxyphenyl)propyl (3-phenoxybenzyl)ether, Traromethrin [(S)-α-cyano-3-phenoxybenzyl (1R,3R)-3-((1'RS)(1',1',2',2'-tetrabromoethyl))-2,2-dimethylcyclopropanecarboxylate] and Silafluofen 4-ethoxylphenyl(3-(4-fluoro-3-phenoxyphenyl)propyl)dimethylsilane.

Other examples are thiadiazine derivatives such as Buprofezin [2-t-butylimino-3 -isopropyl-5-phenyl-1,3,5-thiadiazin-4-one], nitroimidazolidine derivatives such as Imidacloprid [1-(6-chloro-3-pyridylmethl)-N-nitroimidazolidin-2-ylidenamine], Nereis-toxin derivatives such as Cartap [S,S'-(2-dimethylaminotrimethylene)bisthiocarbamate], Thiocyclam [N,N-dimethyl-1,2,3-trithian-5-ylamine], Bensultap [S,S'-2-dimethylaminotrimethylene di(benzenethiosulfonate)], N-cyanoamidine derivatives such as N-cyano-N'-methyl-N'-(6-chloro-3-pyridylmethyl)acetoamidine, chlorinated hydrocarbons such as Endosulfan [6,7,8,9,10, 10-hexachloro-1,5,5a,6,9,9a-hexahydro-6,9-methanobenzo [e]-2,4,3 -dioxathiepin 3-oxide], γ-BHC [1,2,3,4,5,6-hexachlorocyclohexane],1,1 -bis-(chlorophenyl)-2,2,2-trichloroethanol, benzoylphenylurea compounds such as Chlorofluazuron[1-(3,5-chloro-5 -trifluoromethylpyridine-2-yloxy)phenyl)-3-(2,6-difluorobenzoyl)urea], Teflubenzuron [1-(3,5-dichloro-2,4-difluorophenyl)-3 -(2,6-difluorobenzoyl)urea], and Fulphenoxron [1-(4-(2-chloro-4-trifluoromethylphenoxy)-2 -fluorophenyl)-3-(2,6-difluorobenzoyl)urea], formamidine derivatives such as Amitraz [N'-(2,4-dimethylphenyl)-N-((2,4-dimethylphenyl)imino)methyl)-N-methylmethanimidamide], and Chlordimeform [N'-(4-chloro-2-methylphenyl)-N,N-dimethylmethanimidamide], thiourea derivatives such as Diafenthiuron [N-(2,6-diisopropyl-4 -phenoxyphenyl)-N'-t-butylthiourea]; Fipronyl (5-amino-1-(2,6-dichloro-α,α,α-trifluoro-p-tolyl)-4-trifluoromethylsulfinylpyrazole-3-carbonitrite, Bromopropylate [isopropyl 4,4'-diromobenzilate], Tetradifon [2,4,4',5-tetrachlorodiphenyl sulfone], Quinomethionate [6-methyl-2-oxo-1,3-dithiolo-(4,6-b)quinoxaline], Propargite [2-(4-(1,1-dimethylethyl)phenoxy)-cyclohexyl 2-propynylsulfite], Fenbutatin oxide [bis(tris(2-methyl-2-phenylpropyl)tin)oxide], Hexythiazox [(4RS,5RS)-5-(4-chlorophenyl)-N-chlorohexyl-4-methyl-2-oxo-1,3-thiazolidine-3-carboxamide], Chlofentezine [3,6-bis(2-chlorophenyl)-1,2,4,5-tetrazine], Pyridathioben [2-t-butyl-5-(4-t-butylbenzylthio)-4-chloropyridazin-3(2H)-one], Phenpyroxymate [t-butyl(E)-4-((1,3-dimethyl-5-phenoxy-pyrazol-4-yl)methyleneaminooxymethyl)benzoate], Debphenpyrad [N-4-t-butylbenzyl)-4-chloro-3-ethyl-1-methyl-5-pyrazol carboxamide], polynactin complexes including tetranactin, trinactin and dinactin; Milbemectin, Avermectin, Ivermectin, Azadilactin [AZAD] and Pyrimidifen [5-chloro-N-(2-(4-(2-ethoxyethyl)-2,3-dimethylphenoxy)ethyl)-6-ethylpyrimidine-4-amine].

When the hydrazone compound of the present invention is applied as an active ingredient of insecticides, nematocides or acaricides for agricultural use, the amount of application is usually 1 to 1000 g or more, preferably 10 to 100 g per 1000 m$^2$. Emulsifiable concentrates, wettable powders or flowable concentrates of the hydrazone compound of the present invention are diluted with water to a concentration of 10 to 1000 ppm. Granules and dusts are used without any dilution. When the hydrazone compound of the present invention is applied as an active ingredient of insecticides or acaricides for domestic use, the emulsifiable concentrates, wettable powders, flowable concentrates and emulsifiable concentrates are diluted with water to a concentration of 0.01 to 10,000 ppm. Oil sprays, aerosols, fumigants, ULV agents and poisonous baits are used without any dilution.

The amount and concentration for application may be changed optionally according to the type of the formulation used, time, place and method of application, the kind of noxious insects and the damage.

The present invention will be further illustrated by the following Examples, Formulation Examples and Biological Test Examples, which are not to be construed to limit the scope thereof.

The following will describe some examples of the hydrazone compound of the present invention.

EXAMPLE 1

To a solution of 4-chloro-4'-trifluoromethylsulfonyloxy-benzophenone-N'-acetylhydrazone (0.5 g) in N,N-dimethylformamide (4 ml), 0.1 g of a mixture of sodium hydride in oil, which contained 60% (w/w) sodium hydride, was added in one portion at room temperature with stirring. The mixture was stirred at room temperature for 15 minutes to terminate the generation of hydrogen gas, and 1 ml of acetyl chloride was added in one portion. After stirring at room temperature for additional 10 minutes, the reaction mixture was poured into ice water. The aqueous layer was extracted with ethyl acetate, and the combined organic layer was washed with water, diluted hydrochloric acid and saturated sodium bicarbonate solution, and dried over anhydrous magnesium sulfate. The residue obtained after concentration was subjected to silica gel column chromatography to give 0.4 g of 4-chloro-4'-trifluoromethylsulfonyloxy-benzophenone-N',N'-diacetylhydrazone (compound 1).

$n_D^{24.8}$ 1.5432

EXAMPLE 2

To a solution of 4-chloro-4'-trifluoromethylsulfonyloxy-benzophenone (0.5 g) in pyridine (4 ml), 1.5 ml of methoxyacetyl chloride was added in one portion at room temperature with stirring. After stirring at room temperature for additional 3 hours, the reaction mixture was poured into ice water. The aqueous layer was extracted with ethyl acetate, and the combined organic layer was washed with water, diluted hydrochloric acid and saturated sodium bicarbonate solution, and dried over anhydrous magnesium sulfate. The residue obtained after concentration was subjected to silica gel column chromatography to give 0.2 g of 4-chloro-4'-trifluoromethylsulfonyloxybenzophenone-N',N'-di(methoxyacetyl)hydrazone (compound 15) as a resinous product.

H$^1$-NMR (TMS, CDCl$_3$) δ (ppm): 7.0–8.0 (8H), 4.35 (2H, s), 4.33 (2H, s), 3.31 (3H, s), 3.28 (3H, s)

Other examples of the hydrazone compound of the present invention (the substituents R$^1$ and R$^2$ are represented in the formula I) will be shown in Table 1.

TABLE 1

| Compound No. | Physical R$^1$ | R$^2$ | R$^3$ | X | constant |
|---|---|---|---|---|---|
| 1 | CH$_3$ | CH$_3$ | CF$_3$ | Cl | $n_D^{24.8}$ 1.5432 |
| 2 | CH$_3$ | OCH$_2$CH$_3$ | CF$_3$ | Cl | $n_D^{24.8}$ 1.5307 |
| 3 | CH$_3$ | CH$_2$CH$_3$ | CF$_3$ | Cl | $n_D^{25.2}$ 1.5389 |
| 4 | CH$_3$ | CH$_2$OCH$_3$ | CF$_3$ | Cl | m.p., 73–79° C. |
| 5 | OCH$_2$CH$_3$ | OCH$_2$CH$_3$ | CF$_3$ | Cl | $n_D^{24.5}$ 1.5242 |
| 6 | OCH$_2$CH$_3$ | OCH$_3$ | CF$_3$ | Cl | $n_D^{24.5}$ 1.5350 |
| 7 | OCH$_2$CH$_3$ | CH$_2$CH$_3$ | CF$_3$ | Cl | $n_D^{24.5}$ 1.5233 |
| 8 | CH$_2$CH$_3$ | CH$_2$CH$_3$ | CF$_3$ | Cl | $n_D^{24.1}$ 1.5240 |
| 9 | OCH$_3$ | OCH$_3$ | CF$_3$ | Cl | $n_D^{24.0}$ 1.5374 |
| 10 | OCH$_3$ | CH$_3$ | CF$_3$ | Cl | $n_D^{24.0}$ 1.5355 |
| 11 | OCH$_3$ | CH$_2$CH$_3$ | CF$_3$ | Cl | $n_D^{24.0}$ 1.5289 |
| 12 | H | CH$_3$ | CF$_3$ | Cl | $n_D^{23.3}$ 1.5412 |
| 13 | H | CH$_2$CH$_3$ | CF$_3$ | Cl | $n_D^{23.3}$ 1.5369 |
| 14 | CH$_3$ | CH$_2$CN | CF$_3$ | Cl | m.p., 156.2° C. |
| 15 | CH$_2$OCH$_3$ | CH$_2$OCH$_3$ | CF$_3$ | Cl | resinous |
| 16 | CH$_3$ | CH$_3$ | CF$_3$ | Br | |
| 17 | CH$_3$ | OCH$_2$CH$_3$ | CF$_3$ | Br | |
| 18 | CH$_3$ | CH$_2$CH$_3$ | CF$_3$ | Br | |
| 19 | CH$_3$ | CH$_2$OCH$_3$ | CF$_3$ | Br | |
| 20 | CH$_3$ | CH$_2$CN | CF$_3$ | Br | |
| 21 | OCH$_3$ | OCH$_3$ | CF$_3$ | Br | |
| 22 | OCH$_3$ | CH$_2$CH$_3$ | CF$_3$ | Br | |
| 23 | CH$_2$CH$_3$ | CH$_2$CH$_3$ | CF$_3$ | Br | |
| 24 | CH$_2$CH$_3$ | CH$_3$ | CF$_3$ | Br | |
| 25 | CH$_2$CH$_3$ | OCH$_2$CH$_3$ | CF$_3$ | Br | |
| 26 | CH$_2$CH$_3$ | CH$_2$CN | CF$_3$ | Br | |
| 27 | CH$_2$CH$_3$ | CH$_2$OCH$_3$ | CF$_3$ | Br | |
| 28 | OCH$_2$CH$_3$ | OCH$_2$CH | CF$_3$ | Br | $n_D^{24.0}$ 1.5363 |
| 29 | CH$_2$CN | CH$_2$CN | CF$_3$ | Br | |
| 30 | CH$_2$OCH$_3$ | CH$_2$OCH$_3$ | CF$_3$ | Br | |
| 31 | CH$_3$ | CH$_3$ | CH$_3$ | Br | |
| 32 | CH$_3$ | OCH$_2$CH$_3$ | CH$_3$ | Br | |
| 33 | CH$_3$ | CH$_2$CH$_3$ | CH$_3$ | Br | |
| 34 | CH$_3$ | CH$_2$OCH$_3$ | CH$_3$ | Br | |
| 35 | CH$_3$ | CH$_2$CN | CH$_3$ | Br | |
| 36 | OCH$_3$ | OCH$_3$ | CH$_3$ | Br | |
| 37 | OCH$_3$ | CH$_3$ | CH$_3$ | Br | |
| 38 | OCH$_3$ | CH$_2$CH$_3$ | CH$_3$ | Br | |
| 39 | CH$_2$CH$_3$ | CH$_2$CH$_3$ | CH$_3$ | Br | |
| 40 | CH$_2$CH$_3$ | OCH$_2$CH$_3$ | CH$_3$ | Br | |
| 41 | CH$_2$CH$_3$ | CH$_2$CN | CH$_3$ | Br | |
| 42 | CH$_2$CH$_3$ | CH$_2$OCH$_3$ | CH$_3$ | Br | |
| 43 | OCH$_2$CH$_3$ | OCH$_2$CH$_3$ | CH$_3$ | Br | $n_D^{23.8}$ 1.5609 |
| 44 | CH$_2$CN | CH$_3$CN | CH$_3$ | Br | |
| 45 | CH$_2$OCH$_3$ | CH$_2$OCH$_3$ | CH$_3$ | Br | |
| 46 | CH$_3$ | CH$_3$ | CF$_3$ | F | |
| 47 | CH$_3$ | OCH$_2$CH$_3$ | CF$_3$ | F | |
| 48 | CH$_3$ | CH$_2$CH$_3$ | CF$_3$ | F | |
| 49 | CH$_3$ | CH$_2$OCH$_3$ | CF$_3$ | F | |
| 50 | CH$_3$ | CH$_2$CN | CF$_3$ | F | |
| 51 | OCH$_3$ | OCH$_3$ | CF$_3$ | F | |

TABLE 1-continued

| Compound No. | R¹ | R² | R³ | X | Physical constant |
|---|---|---|---|---|---|
| 52 | OCH₃ | CH₂CH₃ | CF₃ | F | |
| 53 | CH₂CH₃ | CH₂CH₃ | CF₃ | F | |
| 54 | CH₂CH₃ | OCH₂CH₃ | CF₃ | F | |
| 55 | CH₂CH₃ | CH₂CN | CF₃ | F | |
| 56 | CH₂CH₃ | CH₂OCH₃ | CF₃ | F | |
| 57 | OCH₂CH₃ | OCH₂CH₃ | CF₃ | F | $n_D^{28.4}$ 1.5055 |
| 58 | OCH₂CH₃ | CH₃ | CF₃ | F | |
| 59 | CH₂CN | CH₂CN | CF₃ | F | |
| 60 | CH₂OCH₃ | CH₂OCH₃ | CF₃ | F | |
| 61 | CH₃ | CH₃ | CH₃ | F | |
| 62 | CH₃ | OCH₂CH₃ | CH₃ | F | |
| 63 | CH₃ | CH₂CH₃ | CH₃ | F | |
| 64 | CH₃ | CH₂OCH₃ | CH₃ | F | |
| 65 | CH₃ | CH₂CN | CH₃ | F | |
| 66 | OCH₃ | OCH₃ | CH₃ | F | |
| 67 | OCH₃ | CH₂CH₃ | CH₃ | F | |
| 68 | CH₂CH₃ | CH₂CH₃ | CH₃ | F | |
| 69 | CH₂CH₃ | CH₃ | CH₃ | F | |
| 70 | CH₂CH₃ | OCH₂CH₃ | CH₃ | F | |
| 71 | CH₂CH₃ | CH₂CN | CH₃ | F | |
| 72 | CH₂CH₃ | CH₂OCH₃ | CH₃ | F | |
| 73 | OCH₂CH₃ | OCH₂CH₃ | CH₃ | F | |
| 74 | OCH₂CH₃ | CH₃ | CH₃ | F | |
| 75 | CH₂CN | CH₂CN | CH₃ | F | |
| 76 | CH₂OCH₃ | CH₂OCH₃ | CH₃ | F | |
| 77 | CH₃ | CH₃ | CF₃ | I | |
| 78 | CH₃ | OCH₂CH₃ | CF₃ | I | |
| 79 | CH₃ | CH₂CH₃ | CF₃ | I | |
| 80 | CH₃ | CH₂OCH₃ | CF₃ | I | |
| 81 | CH₃ | CH₂CN | CF₃ | I | |
| 82 | OCH₃ | OCH₃ | CF₃ | I | |
| 83 | OCH₃ | CH₂CH₃ | CF₃ | I | |
| 84 | CH₂CH₃ | CH₂CH₃ | CF₃ | I | |
| 85 | CH₂CH₃ | OCH₂CH₃ | CF₃ | I | |
| 86 | CH₂CH₃ | CH₂CN | CF₃ | I | |
| 87 | CH₂CH₃ | CH₂OCH₃ | CF₃ | I | |
| 88 | OCH₂CH₃ | OCH₂CH₃ | CF₃ | I | $n_D^{23.6}$ 1.5563 |
| 89 | OCH₂CH₃ | CH₃ | CF₃ | I | |
| 90 | CH₂CN | CH₂CN | CF₃ | I | |
| 91 | CH₂OCH₃ | CH₂OCH₃ | CF₃ | I | |
| 92 | CH₃ | CH₃ | CH₃ | I | |
| 93 | CH₃ | OCH₂CH₃ | CH₃ | I | |
| 94 | CH₃ | CH₂CH₃ | CH₃ | I | |
| 95 | CH₃ | CH₂OCH₃ | CH₃ | I | |
| 96 | CH₃ | CH₂CN | CH₃ | I | |
| 97 | OCH₃ | OCH₃ | CH₃ | I | |
| 98 | OCH₃ | CH₃ | CH₃ | I | |
| 99 | OCH₃ | CH₂CH₃ | CH₃ | I | |
| 100 | OCH₃,OCH₂CH₃ | CH₂CH₃ | CH₃ | I | |
| 101 | CH₂CH₃ | CH₂CH₃ | CH₃ | I | |
| 102 | CH₂CH₃ | OCH₂CH₃ | CH₃ | I | |
| 103 | CH₂CH₃ | CH₂CN | CH₃ | I | |
| 104 | CH₂CH₃ | CH₂OCH₃ | CH₃ | I | |
| 105 | OCH₂CH₃ | OCH₂CH₃ | CH₃ | I | |
| 106 | CH₂CN | CH₂CN | CH₃ | I | |
| 107 | CH₂OCH₃ | CH₂OCH₃ | CH₃ | I | |
| 108 | CH₃ | CH₃ | CH₃ | Cl | |
| 109 | CH₃ | OCH₂CH₃ | CH₃ | Cl | |
| 110 | CH₃ | CH₂CH₃ | CH₃ | Cl | |
| 111 | CH₃ | CH₂OCH₃ | CH₃ | Cl | |
| 112 | CH₃ | CH₂CN | CH₃ | Cl | |
| 113 | OCH₃ | OCH₃ | CH₃ | Cl | |
| 114 | OCH₃ | CH₂CH₃ | CH₃ | Cl | |
| 115 | CH₂CH₃ | CH₂CH₃ | CH₃ | Cl | |
| 116 | CH₂CH₃ | OCH₂CH₃ | CH₃ | Cl | |
| 117 | CH₂CH₃ | CH₂CN | CH₃ | Cl | |
| 118 | CH₂CH₃ | CH₂OCH₃ | CH₃ | Cl | |
| 119 | OCH₂CH₃ | OCH₂CH₃ | CH₃ | Cl | |
| 120 | CH₂CN | CH₂CN | CH₃ | Cl | |
| 121 | CH₂OCH₃ | CH₂OCH₃ | CH₃ | Cl | |

The following will hereinafter describe Formulation Examples of the hydrazone compound of the present invention. In these Formulation Examples, the compounds are designated by the corresponding numbers in Table 1 and "parts" are by weight unless otherwise stated.

Formulation Example 1

Emulsifiable concentrates

Ten parts of each of the compounds 1 to 121 are separately dissolved in 35 parts of xylene and 35 parts of dimethylformamide. Each of these mixtures is mixed with 14 parts of polyoxyethylene styrylphenyl ether and 6 parts of calcium dodecylbenzenesulfonate, and the resultant mixture is stirred sufficiently to give 10% emulsifiable concentrates for each compound.

Formulation Example 2

Wettable powders

Twenty parts of each of the compounds 1 to 121 are separately added to a mixture of 4 parts of sodium lauryl sulfate, 2 parts of calcium lignin sulfonate, 20 parts of synthetic hydrated silicon hydroxide fine powder and 54 parts of diatomaceous earth, and the resultant mixture is stirred with a mixer to give 20% wettable powders for each compound.

Formulation Example 3

Granules (in case of solid technical product)

To 5 parts of each of the compounds 4 and 14 are added 5 parts of synthetic hydrated silicon hydroxide fine powder, 5 parts of sodium dodecylbenzenesulfonate, 30 parts of bentonite and 55 parts of clay, and the resultant mixture is stirred sufficiently. Then, a suitable amount of water is added to the mixture, which is further stirred, granulated with a granulator and then air-dried to give a 5% granular for each compound.

Formulation Example 4

Granules (in case of liquid technical product)

To 5 parts of each of the compounds 1 to 3, 5–13, 28, 43, 57 and 88 are added 5 parts of sodium dodecylbenzenesulfonate, 30 parts of bentonite and 60 parts of clay, and the resultant mixture is stirred sufficiently. Then, a suitable amount of water is added to the mixture, which was further stirred, granulated with a granulator and then air dried to give a 5% granular for each compound.

Formulation Example 5

Dusts

One part of each of the compounds 1 to 121 separately dissolved in a suitable amount of acetone is mixed with 5 parts of synthetic hydrated silicon hydroxide fine powder, 0.3 parts of PAP and 93.7 parts of clay. Then, the resultant mixture was stirred with a mixer and acetone is evaporated to give 1% dusts for each compound.

Formulation Example 6

Flowables (in case of solid technical product)

Twenty parts of each of the compounds 4 and 14 are separately mixed with 1.5 parts of sorbitan trioleate and 28.5 parts of an aqueous solution containing 2 parts of polyvinyl alcohol, and the resultant mixture is pulverized into fine particles having a particle size of not more than 3 μm with a sand grinder. Each of these mixtures was mixed with 40 parts of an aqueous solution containing 0.05 parts of xanthan gum and 0.1 parts is of aluminum magnesium silicate, and then mixed with 10 parts of propylene glycol to give 20% water-based suspensions for each compound.

Formulation Example 7

Flowables (in case of liquid technical product)

Ten pans of each of the compounds 1 to 3, 5–13, 28, 43, 57 and 88 are separately mixed with an aqueous solution containing 6 parts of polyvinyl alcohol, and the resultant mixture is stirred with a mixer to give a dispersing agent. The dispersing agent is mixed with 40 parts of an aqueous solution containing 0.05 parts of xanthan gum and 0.1 parts of aluminum magnesium silicate, and then mixed with 10 parts of propylene glycol to give 10% water-based emulsions for each compound.

Formulation Example 8

Oil solutions

First, 0.1 parts of each of the compounds 1 to 121 are separately dissolved in 5 parts of xylene and 5 parts of trichloroethane. The resultant solution was mixed with 89.8 parts of deodorized kerosine to give 0.1% oil solutions for each compound.

Formulation Example 9

Oil-based aerosols

First, 0.1 parts of each of the compounds 1 to 121, 0.2 parts of tetramethrin, 0.1 parts of d-phenothrin and 10 parts of trichloroethane are dissolved in 59.6 parts of deodorized kerosine, and an aerozol vessel is filled with the resultant solution. Then, the vessel is equipped with a valve, through which 30 parts of a propellant (liquefied petroleum gas) are charged under pressure to give an oil-based aerosol of each compound.

Formulation Example 10

Water-based aerosols

An aerosol vessel is filled with 50 parts of pure water and a mixture of 0.2 parts of each of the compounds 1 to 121, 0.2 parts of d-allethrin, 0.2 parts of d-phenothrin, 5 parts of xylene, 3.4 parts of deodorized ketosine and 1 part of an emulsifier [ATMOS 300 (registered trade mark by Atlas Chemical Co.)]. Then, the vessel is equipped with a valve, through which 40 parts of a propellant (liquefied petroleum gas) are charged under pressure to give a water-based aerosol of each compound.

The following Biological Test Examples will illustrate that hydrazone compounds of the present invention are useful as an active ingredient of insecticides. In these Biological Test Examples, the compounds are designated by the corresponding numbers in Table 1.

Biological Test Example 1

Insecticidal test on *Spodoptera litura*

An emulsion was prepared from the test compound according to Formulation Example 1. Then, 13 g of an artificial diet for *Spodoptera litura* prepared in a polyethylene cup having a diameter of 11 cm beforehand was impregnated with 2 ml of a solution (500 ppm) prepared by dilution of the emulsion with water. Ten fourth-instar larvae of *Spodoptera litura* were set free in the cup. After six days, the survival of larvae was examined to determine the mortality.

As a result, it was found that the compounds 1–15, 28, 43, 57 and 88 exhibited the mortality of 100%.

In the non-treated field, the mortality was 0%.

Biological Test Example 2

Ovicidal and larvicidal tests on *Plutella xylostella*

An emulsion was prepared from the test compound according to Formulation Example 1. Then, four sprouted Japanese radishes which have been harvested for five to six days after seeding, i.e., two Japanese radishes on which 100 to 150 eggs of *Plutella xylostella* were laid and two Japanese radishes on which no egg was laid were dipped in a solution (50 ppm) obtained by dilution of the emulsion with water and air-dried, and then put in a polyethylene cup having a diameter of 5.5 cm. After five days, the hatching and the survival of larva were examined to determine the ovicidal and larvicidal rates.

The evaluation was conducted according to the following criteria:

a: Ovicidal or larvicidal rate of more than 99% b: Ovicidal or larvicidal rate of 90 to 99% c: Ovicidal or larvicidal rate of less than 90%

As a result, it was found that the compounds 1–4, 6, 8, 10–14, 43, 57 and 88 were evaluated as "a".

In the non-treated field, they were evaluated as "c".

Biological Test Example 3

Insecticidal test on larvae of *Nilaparvata lugens*

A stalk of rice having a length of about 5 cm was dipped in a solution (500 ppm) obtained by dilution with water of the emulsion prepared from the test compound according to Formulation Example 1. After air cooling, the stalk of rice was put in a polyethylene cup having a diameter of 5.5 cm, in which a filter paper (diameter: 5.5 cm) containing 1 ml of water was laid on the bottom, and about 30 larvae of *Nilaparvata lugens* were set free in the cup. After six days, the survival of larvae was examined to determine the mortality.

The evaluation was conducted according to the following criteria:

a: No survival larvae is observed.

b: Not more than 5 survival larvae are observed.

c: Not less than 6 survival larvae are observed.

As a result, it was found that the compounds 4, 6, 7, 9 and 12 were evaluated as "a".

In the non-treated field, they were evaluated as "c".

Biological Test Example 4

Insecticidal test on larvae of *Diabrotica undecimpunctata*

On the bottom of a polyethylene cup having a diameter of 5.5 cm, a filter paper having the same diameter was laid, and 1 ml of a solution (50 ppm) prepared by dilution with water of the emulsion according to Formulation Example 1 was dropped on the filter paper. Then, about 30 eggs of *Diabrotica undecimpunctata* were put on the filter paper, and a sprouted corn as a diet was put in the cup. After eight days, the survival of hatched larvae was examined.

a: Mortality of more than 99% b: Mortality of 99 to 90% c: Mortality of less than 90%

As a result, it was found that the compounds 1–4, 6–15, 28 and 57 were evaluated as "a".

In the non-treated field, they were evaluated as "c".

Biological Test Example 5

Insecticidal test on larvae of *Musca domestica* Linne)

On the bottom of a polyethylene cup having a diameter of 5.5 cm, a filter paper of the same diameter was laid, and 0.7 ml of a diluted solution of the emulsion (500 ppm) prepared from the test compound according to Formulation Example 1 in water was dropped on the filter paper, and 30 mg of sucrose as a diet was put in the cup. Then, 10 male adults of *Musca domestica* Linne were set free in the cup, and a lid was put on the cup. After one day, the survival of male adults was examined to determine the mortality.

As a result, it was found that the compounds 1–3, 7, 8, 11–13 and 15 exhibited the mortality of 100%.

In the non-treated field, the mortality was 0%.

Biological Test Example 6

Insecticidal test on larvae of *Blattella germanica*

On the bottom of a polyethylene cup having a diameter of 5.5 cm, a filter paper having the same diameter was laid, and 0.7 ml of a diluted solution of the emulsion (500 ppm) prepared from the test compound according to Formulation Example 1 in water was dropped on the filter paper, and 30 mg of sucrose as a diet was put in the cup. Then, 10 male adults of *Blattella germanica* were set free in the cup, and a lid was put on the cup. After six days, the survival of male adults was examined to determine the mortality.

As a result, it was found that the compounds 1, 2, 4–7, 9–15, 43, 57 and 88 exhibited the mortality of 100%.

In the non-treated field, the mortality was 0%.

Biological Test Example 7

Insecticidal test on *Culex pipiens pallens*

An emulsion was prepared from the test compound according to Formulation Example 1. Then, the emulsion was diluted with water and 0.7 ml of the diluted emulsion was added to 100 ml of deionized water to give a solution (concentration of the active ingredient: 3.5 ppm). Twenty final instar larvae of *Cutex pipiens pallens* were set free in the solution. After one day, the mortality was examined.

The effect was evaluated according to the following criteria:

a: Mortality of not less than 90% b: Mortality of 10 to 90% c: Mortality of less than 10%

As a result, it was found that the compounds 1–15, 28, 57 and 88 were evaluated as "a".

Biological Test Example 8

Insecticidal test on *Aphis gossypii*

Thirty milliliters (500 ppm) of a solution prepared by dilution with water of the emulsion of the test compound according to Formulation Example 1 were sprayed to a cotton of primary leaf stage planted in a polyethylene cup, on which about 20 larvae of *Aphis gossypii* were parasitic.

After 7 days, the number of survival of the larvae was counted, and the prevention rate was determined by comparison of the numbers of the survival of the individuals of the treated and the untreated cases.

As a result, it was found that the prevention rate was 98.7% for the compound 1 and 57.3 % for the compound A as a comparative example in Table 2.

Biological Test Example 9

Acute toxicity by oral application to mice

Each of the test compounds, i.e., compound 1 and 5 of the present invention and compounds A and B for comparison, was diluted to a predetermined concentration with corn oil. After twenty-hour fasting, 0.1 ml of the diluted solution per 10 g weight was forcibly applied to the stomach of each ICR male 6-week old mouse (weight: 24 to 31 g). The mice was given food and water since four hours after the application, and kept in a cage, the mortality was examined for the mice (5 mice/group). The results are shown in Table 2.

TABLE 2

| Test compound | Dosage (mg/Kg) | Mortality (%) |
| --- | --- | --- |
| Compound 1 | 30 | 0 |
| Compound 5 | 30 | 0 |
| Compound A* | 30 | 100 |

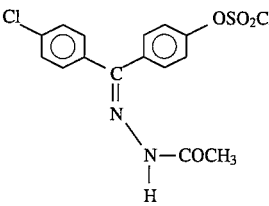

| Compound B* | 30 | 40 |

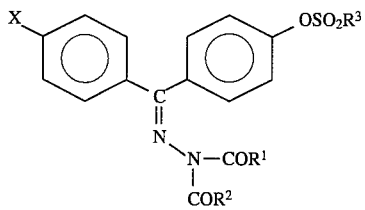

*Compound A is embraced in the U.S. Pat. No. 4,344,893 and compound B is disclosed as compound No. 83 in column 20 in the same U.S. Pat.

What is claimed is:

1. A hydrazone compound of the formula I:

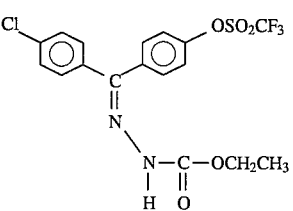

wherein $R^1$ and $R^2$ are the same or different and are independently hydrogen, $C_1$–$C_2$ alkyl, $C_1$–$C_2$ alkoxy, methoxymethyl or cyanomethyl, with the proviso that the $R^1$ and $R^2$ are not simultaneously hydrogen; $R^3$ is trifluoromethyl or methyl; and X is halogen.

2. A hydrazone compound according to claim 1, wherein the $R^3$ is trifluoromethyl.

3. A hydrazone compound according to claim 2, wherein X is chlorine.

4. A hydrazone compound according to claim 3, which is 4-chloro-4'-trifluoromethylsulfonyloxybenzophenone-N', N'-diacetylhydrazone.

5. A hydrazone compound according to claim 3, which is 4-chloro-4'-trifluoromethylsulfonyloxybenzophenone-N', N'-di(ethoxycarbonyl)hydrazone.

6. A hydrazone compound according to claim 3, which is 4-chloro-4'-trifluoromethylsulfonyloxybenzophenone-N', N'-di(methoxyacetyl)hydrazone.

7. A hydrazone compound according to claim 3, which is 4-chloro-4 -trifluoromethylsulfonyloxybenzophenone-N', N'-di(cyanomethyl)hydrazone.

8. An insecticide comprising the hydrazone compound according to claim 1 as an active ingredient.

9. A method for controlling noxious insects, which comprises applying an effective amount of the hydrazone compound according to claim 1 to the locus where insect pests propagate.

* * * * *